(12) United States Patent
Duck et al.

(10) Patent No.: US 7,528,400 B2
(45) Date of Patent: May 5, 2009

(54) OPTICAL TRANSLATION OF TRIANGULATION POSITION MEASUREMENT

(75) Inventors: Graham I. Duck, North Vancouver (CA); Michael K. Y. Hughes, Vancouver (CA)

(73) Assignee: Honeywell ASCA Inc., Ontario (CA)

( * ) Notice: Subject to any disclaimer, the term of this patent is extended or adjusted under 35 U.S.C. 154(b) by 167 days.

(21) Appl. No.: 11/595,061

(22) Filed: Nov. 10, 2006

(65) Prior Publication Data

US 2007/0145307 A1 Jun. 28, 2007

Related U.S. Application Data

(60) Provisional application No. 60/753,691, filed on Dec. 22, 2005.

(51) Int. Cl.
*G01B 11/06* (2006.01)
*G01C 3/10* (2006.01)
*G01S 17/48* (2006.01)

(52) U.S. Cl. ............... 250/559.23; 250/559.27; 250/559.31; 356/623; 356/631

(58) Field of Classification Search ............ 250/559.23, 250/559.27, 559.31; 356/631, 623
See application file for complete search history.

(56) References Cited

U.S. PATENT DOCUMENTS

| | | | | |
|---|---|---|---|---|
| 4,168,126 A * | 9/1979 | Altman et al. | ............. | 356/640 |
| 4,276,480 A * | 6/1981 | Watson | .............. | 250/559.1 |
| 4,585,345 A * | 4/1986 | Inoue | .............. | 356/455 |
| 4,879,471 A * | 11/1989 | Dahlquist | ............. | 250/359.1 |
| 5,094,535 A * | 3/1992 | Dahlquist et al. | ............. | 356/451 |
| 5,166,748 A * | 11/1992 | Dahlquist | ............. | 356/451 |
| 5,210,593 A | 5/1993 | Kramer | | |
| 5,581,353 A * | 12/1996 | Taylor | ............. | 356/631 |
| 5,737,084 A * | 4/1998 | Ishihara | ............. | 356/609 |
| 5,892,679 A * | 4/1999 | He | ............. | 700/29 |
| 6,038,028 A * | 3/2000 | Grann et al. | ............. | 356/630 |
| 6,059,931 A * | 5/2000 | Hu et al. | ............. | 162/198 |
| 6,080,278 A * | 6/2000 | Heaven et al. | ............. | 162/198 |
| 6,092,003 A * | 7/2000 | Hagart-Alexander et al. | ............. | 700/129 |
| 6,149,770 A * | 11/2000 | Hu et al. | ............. | 162/199 |
| 6,281,679 B1 | 8/2001 | King | | |
| 6,373,978 B1 | 4/2002 | Ishihara | | |
| 6,466,839 B1 * | 10/2002 | Heaven et al. | ............. | 700/128 |
| 6,805,899 B2 * | 10/2004 | MacHattie et al. | ............. | 427/8 |

(Continued)

FOREIGN PATENT DOCUMENTS

DE      3932844 A1      4/1991

(Continued)

*Primary Examiner*—John R Lee
(74) *Attorney, Agent, or Firm*—Cascio Schmoyer & Zervas

(57) ABSTRACT

An optical translation technique for moving the interrogation spot at which a triangulation system measures the displacement of a target is disclosed. In normal operation of the laser triangulation sensor, an incident laser beam is projected from a sensor head onto a surface of a web that is facing the sensor head. Radiation is reflected from the surface and detected by the sensor. The distance from the sensor head to the web surface is calculated by triangulation. With optical translation, both the incident ray path and the captured ray path are translated with a plurality of high refractive index geometries such that the nominal functioning of the triangulation sensor remains undisturbed. The optimal position on the sheet wherein the interrogation spot will be located can be ascertained.

23 Claims, 7 Drawing Sheets

U.S. PATENT DOCUMENTS

| | | |
|---|---|---|
| 6,853,543 B1 * | 2/2005 | Moore et al. ............... 361/680 |
| 6,936,137 B2 | 8/2005 | Moeller |
| 6,967,726 B2 | 11/2005 | King |
| 7,199,884 B2 * | 4/2007 | Jasinski et al. ............. 356/632 |
| 2007/0145307 A1 * | 6/2007 | Duck et al. ............ 250/559.01 |
| 2007/0153286 A1 * | 7/2007 | Hughes et al. ............. 356/451 |

FOREIGN PATENT DOCUMENTS

DE  102004003329 B3  10/2005

* cited by examiner

OPTICAL TRANSLATION OF TRIANGULATION POSITION MEASUREMENT

REFERENCE TO RELATED APPLICATIONS

This application claims priority to U.S. Provisional Application 60/753,691 that was filed on Dec. 22, 2005.

FIELD OF THE INVENTION

The present invention relates generally to techniques for non-contacting thickness or caliper measurements of moving sheets such as paper and more particularly to methods of enabling a single point triangulation caliper sensor to optically translate the spot at which the triangulation system measures the displacement of a target. The invention facilitates optimization of various parameters of the caliper sensor and permits determination of the desired position on a moving sheet where the interrogation spot should be.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Many factors influence the rate at which water is removed which ultimately affects the quality of the paper produced.

It is well known to continuously measure certain properties of the paper material in order to monitor the quality of the finished product. These on-line measurements often include basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge.

It is conventional to measure the caliper of sheet material upon its leaving the main dryer section or at the take-up reel with scanning sensors. Such measurements may be used to adjust the machine operation toward achieving desired parameters. Numerous methods exist for measuring the thickness of a moving web or sheet, such as paper. Two of the most common techniques include direct thickness measurements using contacting glides or shoes, which skim along the two surfaces of the web, and non-contacting inferential method in which radiation absorption by the web is used to determine the weight per unit area of the web and the thickness is thereafter inferred, provided the density of the material is known with sufficient precision. Many variations and improvements to these methods exist, but each of the techniques has underlying drawbacks.

The contacting method is subject to three fundamental types of problems. First, the method can be limited by the strength of the material being measured. With fragile sheets such as tissue, for example, there is a tendency for the contacting shoes to snag deviations in the sheet surface, causing flaws in the sheet or even causing the sheet to tear. Second, the sheet itself can damage a contacting caliper sensor due either to abrasive wear on the contacting elements or to physical damage arising during sheet breaks. For caliper sensors that traverse the sheet, damage can also be caused when the sensor crosses the sheet edge. Third, the accuracy of contacting sensors can be adversely affected by the buildup of contaminants on the contacting elements, as may occur with coated or filled sheets or sheets containing recycled materials.

The non-contacting inferential thickness measurement methods avoid many of the problems of the contacting methods but are subject to a new set of problems. Several patents have suggested that use of lasers to measure the thickness of a moving web may be a promising option compared to the other methods available. One such system is described in U.S. Pat. No. 5,210,593 to Kramer and another is described in U.S. Pat. No. 4,276,480 to Watson. In both systems, the laser caliper apparatus comprises a laser source that is positioned on both sides of the web whose light is directed onto the web surface and subsequently reflected to a receiver. The characteristics of the received laser signal are thereafter used to determine the distance from each receiver to the web surface. These distances are added together and the result is subtracted from a known value for the distance between the two laser receivers. The result represents the web's thickness.

The above non-contacting approaches to thickness measurements have the desirable feature of eliminating many of the disadvantages of the contacting method and the non-contacting inferential methods. However, there are difficulties with previous non-contacting techniques that can limit their usefulness to relatively low-accuracy applications.

One of the problems is that the web may not always be perpendicular to the incident light since the web has a tendency to bounce or develop intermittent wave-like motion. If the web is non-perpendicular to the incident light and the light beams from two opposing light sources are not directed to exactly the same spot on the sheet, substantial error in measurement can occur. This is caused by a number of factors. First, actual web thickness variations from the first laser's measurement spot to the second laser's measurement spot can cause an incorrect thickness measurement. Second, if the web is not perpendicular to the incident light, the measurement technique will cause an error in the thickness value proportional to the web's angle and to the displacement on the sheet surface between the two measurement spots. Bouncing or oscillation of the web can further exacerbate this error.

U.S. Pat. No. 6,281,679 to King et al. describes a non-contact web thickness measurement system which has distance determining means on opposite sides of the web. The system includes a caliper sensor that is capable of accurate on-line web thickness measurements even when continuously scanning the system across the web. The air clamp can be operated such that air flow will force the machine direction moving sheet to a minimum displacement position as seen by the laser underneath the air clamp (and a maximum for the other). The air clamp is largely designed such that the sheet displacement is largely invariant in the cross direction. At this position, small x-y displacements introduce minimal error to the measurement. This assumes that sheet thickness is largely determined by paper machine properties and that the microstructure of the paper is not considered. This is true when average measurements are made which is generally the case for practical measurements on moving sheets.

When employed to measure the thickness of paper, the caliper sensor is typically stationed at the dry end of the papermaking machine. It has been assumed that the sheet's surface is perpendicular to the laser beams and relatively flat along the machine direction in the region where the paper passes through the caliper sensor so that the ideal interrogation spot is directly above and below the upper and lower sensor heads respectively. However, it has been discovered that the sheet's surface is not sufficiently planar. The result was that the ideal interrogation spot is often located on a part of the surface of the sheet that did not yield precise thickness measurements. Moreover, it is difficult to change the location of the interrogation spot since that would entail disassembling and physically moving the caliper sensor either upstream or downstream from its original position.

SUMMARY OF THE INVENTION

The present invention is based in part on the development of an optical translation technique for moving the interrogation spot at which a triangulation sensor measures the displacement of a target such as a moving web or sheet of paper. In normal operations of a laser triangulation sensor, an incident laser beam or ray is projected from a sensor head onto a surface of a web that is facing the sensor head. Radiation reflected from the surface is detected or captured by a detector. The distance from the sensor head to the web surface is calculated by triangulation. With the inventive optical translation technique, both the incident ray and the captured ray are translated with one or more transparent substrates, e.g., a plurality of glass geometries, such that the nominal functioning of the triangulation sensor is undisturbed. Optical translation permits adjustments to the interrogation spot without having to physically move the triangulation sensor.

Caliper sensors employ triangulation sensors to continuously monitor the thickness of a moving or changing target. The caliper sensor can include an air clamp that stabilizes the moving target so the location on the surface, where the interrogation spot of the triangulation sensor is directed, remains stationary to ensure that the caliper sensor yields accurate thickness measurements. During operations of a sheet forming process such as in papermaking, it may be desirable to adjust the traveling paper's position by modifying the force that is exerted on the sheet by the air clamp when practicable taking into consideration the degree of sheet flutter and resistance to tension changes. (In cases, where it is not possible to move the minimum to the desired locations, it would be necessary to physically moving the laser devices.) Once the new position of the sheet has been established, the proper location of the interrogation spot on the sheet can be determined with the inventive optical translation technique. Similarly, should the contour of a moving sheet of paper deviate or shift during operation of the papermaking machine so that the original interrogation spot is no longer at an optimum location, optical translation maneuvers the interrogation spot to a better location without the need to physically move the caliper sensor. In either case, optical translation allows the caliper sensor to function normally without having to physically move the caliper sensor.

In one aspect, the invention is directed to a triangulation sensing device for measuring the distance from a target such as a moving web or sheet that includes:

a sensor head that is disposed adjacent the target wherein the sensor head includes (i) a source of incident radiation that is directed to a surface of the target and (ii) means for detecting reflected radiation from an interrogation spot on the surface of the target;

means for optically translating the incident radiation such that the interrogation spot is moved to a desired position; and means for optically translating the reflected radiation from the interrogation spot at the desired position such that the reflected radiation is detected by the means for detecting reflected radiation. A feature of the invention is that even though the reflected beam is translated, the distance measurement remains correct. Without compensation, the reflected beam would usually still be detected but a considerable portion of the beam would be lost from the side of the sensor device.

In another aspect, the invention is directed to a system, for measurement of the thickness of a target having a first surface and a second surface, that includes:

a first sensor head that is disposed adjacent the first surface of the target wherein the first sensor head includes (i) a first source of first incident radiation that is directed to the first surface of the target and (ii) first means for detecting first reflected radiation from a first interrogation spot on the first surface of the target;

means for optically translating the first incident radiation such that the first interrogation spot is moved to a first desired position on the first surface of the target;

means for optically translating the first reflected radiation from the first interrogation spot at the first desired position such that the first reflected radiation is detected by the first means for detecting first reflected radiation;

a second sensor head that is disposed adjacent the second surface of the target wherein the second sensor head includes (i) a second source of second incident radiation that is directed to the second surface of the target and (ii) second means for detecting second reflected radiation from a second interrogation spot on the second surface of the target;

means optically translating the second incident radiation such that the second interrogation spot is moved to a second desired position on the second surface of the target;

means for optically translating the second reflected radiation from the second interrogation spot at the second desired position such that the second reflected radiation is detected by the second means for detecting second reflected radiation; and means for measuring the distance from the first sensor head to the second sensor head.

In a further aspect, the invention is directed to a method of determining the position of a target that includes the steps of:

(a) providing a triangulation sensing device for measuring distance that comprises a sensor head that is disposed adjacent the target wherein the sensor head includes (i) a source of incident radiation that is directed to a surface of the target and (ii) means for detecting reflected radiation from an interrogation spot on the surface of the target;

(b) optically translating the incident radiation such that the interrogation spot is moved to a desired position on the target surface;

(c) optically translating the reflected radiation from the interrogation spot such that the reflected radiation is detected by the means for detecting reflected radiation; and (d) determining the position of the interrogation spot, e.g., height of the spot relative to the triangulation sensing device.

DESCRIPTION PREFERRED EMBODIMENTS

The present invention is directed to novel optical translation techniques that can be applied to any distance measuring device that employs the principle of triangulation. These distance measuring devices include, for example, conventional laser triangulation sensors that have a solid-state laser source that emits a beam onto a point on a surface of a target being measured and a detector that is arranged along an oblique ray that images the laser spot from the point and measures its reflected angle with respect to its optic axis. The invention is particularly suited for incorporation into distance measuring devices to move the interrogation spot on the target being measured. Thus while the invention will be described in relation to a paper thickness or caliper sensor that is equipped with sensor heads with laser triangulation sensors, it is understood that the invention can be employed in other devices and applications as well.

Non-contacting caliper sensors such as that disclosed in U.S. Pat. No. 6,281,679 to King et al., which is incorporated herein by reference, include upper and lower heads with a laser triangulation device in each head. The caliper of a moving sheet that travels between the two heads is determined by identifying the positions of the upper and lower surfaces of the sheet with the laser triangulation devices and subtracting the results from a measure of the separation between the upper and lower heads.

Figure 1A:
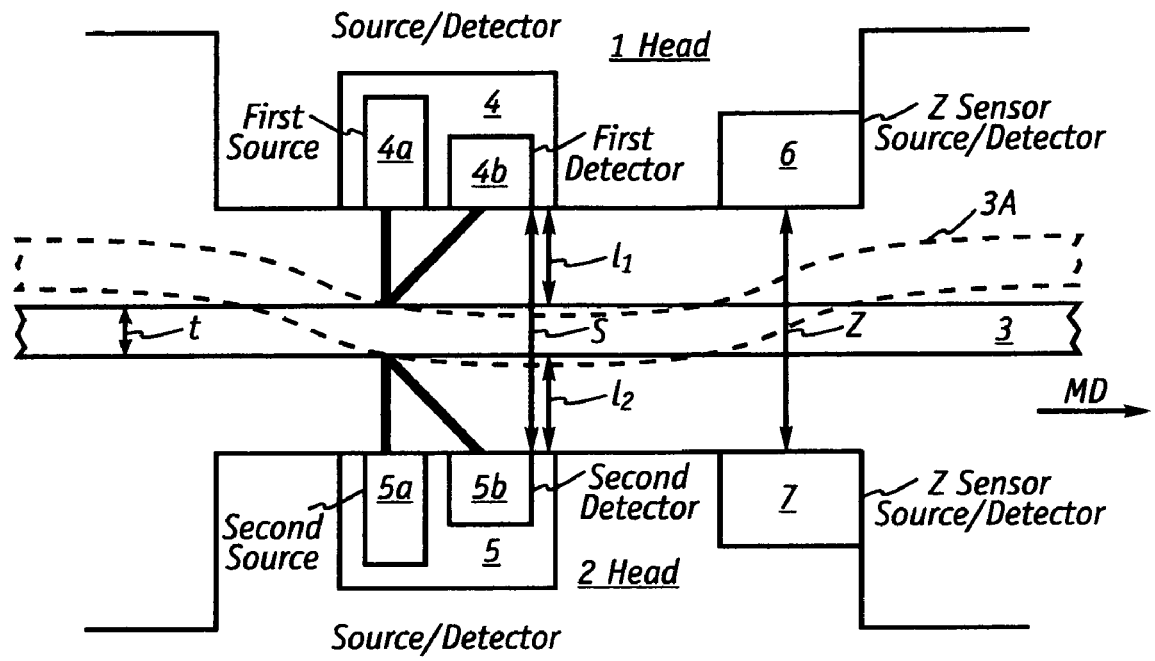
FIGS. 1A, 1B, and 1C are cross sectional schematic views of a caliper measurement device.

FIG. 1A illustrates a representative non-contacting caliper sensor system that includes first and second enclosures (hereafter called "scanner heads" or "heads"), 1 and 2 respectively, which contain various sensor devices for measuring qualities, characteristics, or features of a moving web of material identified as 3. Heads 1 and 2 lie on opposite sides of web or sheet 3, and, if the measurement is to be performed in a scanning manner across the web in the cross direction (CD), the heads are aligned to travel directly across from each other as they traverse the moving web which is moving in the machine direction (MD). A first source/detector 4 is located in first head 1. A second source/detector 5 is located in second head 2. Source/detectors 4 and 5 comprise closely-spaced first and second sources 4a and 5a, respectively, and first and second detectors 4b and 5b, respectively, arranged so that measurement energy from first source 4a and interacting with a first surface of web 3 will return, at least in part to first detector 4b, and measurement energy from second source 5a and interacting with the opposite, or second surface, of web 3 will return, at least in part to second detector 5b. In this particular system, the web-facing surfaces of the first and second sources comprise a first and second reference location, respectively.

The source and detector preferably comprise a laser triangulation source and detector, collectively being referred to as an interrogation laser. The source/detector arrangement is referred to generally as a distance determining means. From the measured path length from the source to the detector, values for the distance between each distance determining means and a measurement or interrogation spot on one of the web surfaces may be determined. The heads 1 and 2 are typically fixed in the position so that the interrogations spots do not move in the machine direction even as the heads are scanned in the cross direction.

For first distance determining means 4, the detected distance value between the distance determining means and a first measurement spot on the web surface will be referred to as $l_1$ and for second distance determining means 5, the detected distance value between the distance determining means and a second measurement spot on the opposite web surface will be referred to as $l_2$, as shown in FIG. 1A. For accurate thickness determinations, the first and second measurement spots (or interrogation spots) must be at the same point in the x-y plane, but on opposite sides of the web, i.e. the measurement spots will be separated by the web thickness. In an ideal static situation, the separation, s, between first and second distance determining means 4 and 5 would be fixed, resulting in a calculated value for web thickness, t, of: $t=s-(l_1+l_2)$. It should be noted that the surface of may be indistinct and that the measurement spot may be centered under the surface of the web. This can be corrected with another offset which is usually experimentally determined.

In practice, separation s can vary. To correct for this inconstancy in the separation s, a dynamic measurement of the spacing between the scanning heads is provided by a z-sensor means, which measures a distance z, between a z-sensor source/detector 6, located in the first head 1, and a z-sensor reference 7, located in the second head 2.

Figure 1B:
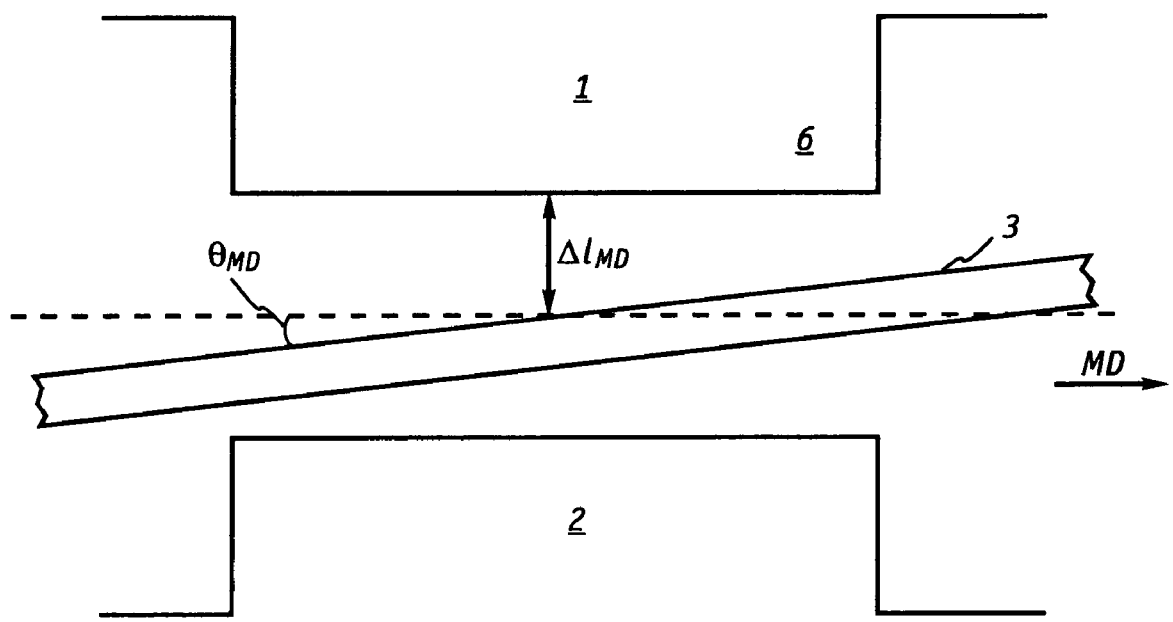
Figure 1C:
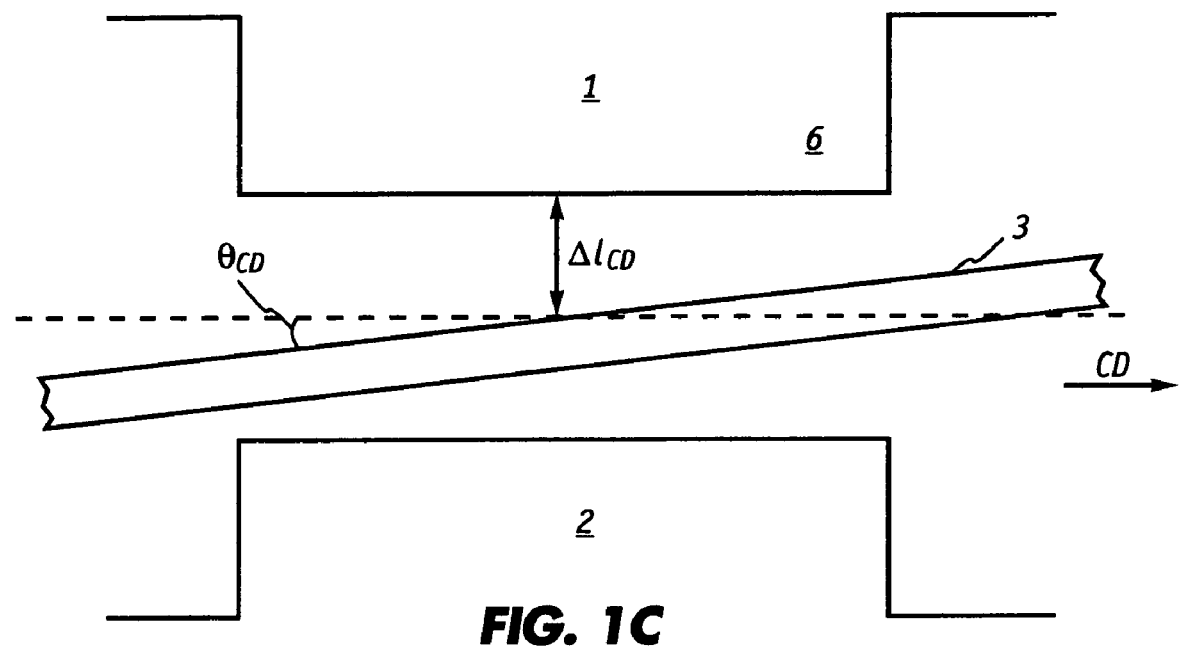

In addition, because the scanner heads do not retain perfect mutual alignment as a sheet scans between them, it is necessary to keep the sheet flat so that small head misalignments do not translate into erroneous caliper readings, i.e., caliper error due to head misalignment and sheet angle. This phenomenon is illustrated in FIGS. 1B and 1C which show the relative positions of upper scanner head 1, lower scanner head 2, and web 3 in the MD and CD, respectively. The caliper error, $\Delta t$, can be estimated as $\Delta t = \Delta l_{MD} \theta_{MD} + \Delta l_{CD} \theta_{CD}$, Equation 1), where $\Delta l_{MD}$ and $\Delta l_{CD}$ are the relative misalignments in the machine direction and cross direction, respectively, and $\theta_{MD}$ and $\theta_{CD}$ are the angles of the sheet surface parallel to the MD and CD directions.

Referring to FIG. 1A, the portion of the moving web 3 that traverses between scanner heads 1 and 2 is illustrated as being planar; however, in practice over time the web may exhibit a non-linear pattern or wave-like as depicted by web 3A. This wave-like pattern is the result of a confluence of various external forces. Typically, the non-linear pattern will have a minimal point and, in order to provide consistent and precise caliper measurements, it is preferred that the interrogations spots be located at the minimal point of the web 3A as illustrated. However, it is seldom the case that the minimal point which develops in the non-linear web coincides with the original locations of the interrogations spots which are fixed once the caliper sensor is installed.

Figure 2A:
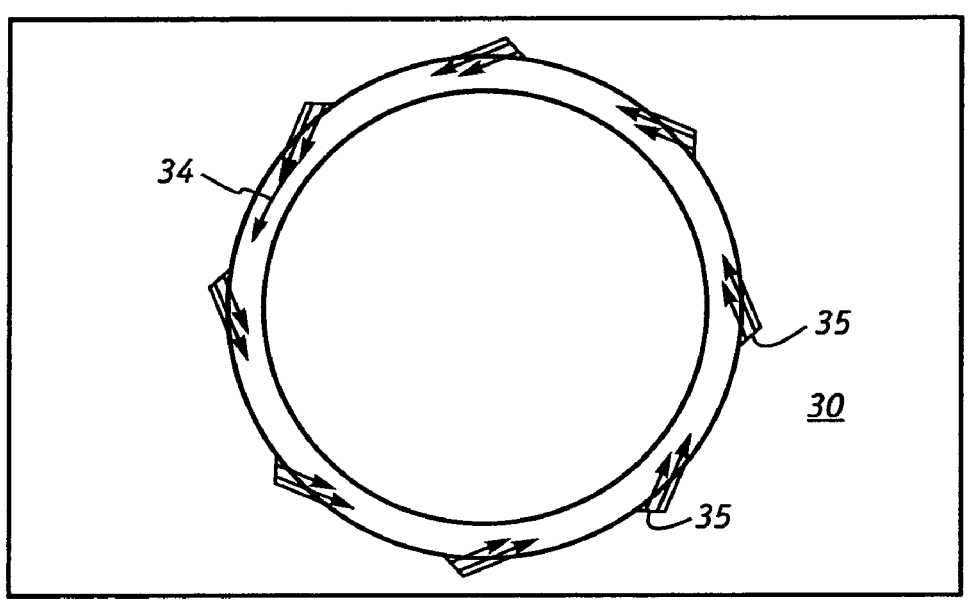
FIG. 2A illustrates the clamp plate from above with the web removed.
Figure 2B:
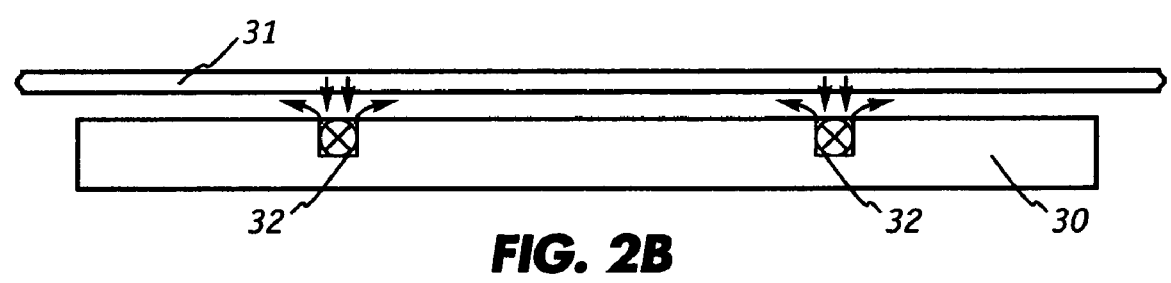
FIG. 2B is a side view of an air clamp plane and the forces applied to the web when the air flow is operational.

The thickness measurement system can also include an air-bearing stabilizer as shown in FIGS. 2A and 2B. The web stabilizer is based on a vortex of moving air, hereafter referred to as an "air clamp" and includes a clamp plate 30, mounted near where web 31 is to be stabilized, and a circular air channel 32 in clamp plate 30 coincident with its upper surface. When air 34 is introduced into the circular air channel 32, a field of low pressure is created over the channel. Web 31 is pulled toward this ring of low pressure. The air may be introduced, for example, via a series of air orifices 35, in the side of circular air channel 32. Simultaneously, a pocket of higher pressure is created by escaping air from channel 32 in the region adjacent the channel. This area of high pressure counteracts the attractive force of the low-pressure area above the channel. By balancing these two forces, the average path of the web may be maintained in a fixed position relative to the channel, without requiring any part of the air clamp come into physical contact with the web. As is apparent, the height of the web or sheet between the upper and lower sensor heads can be adjusted by regulating the air clamp.

Figure 2C:
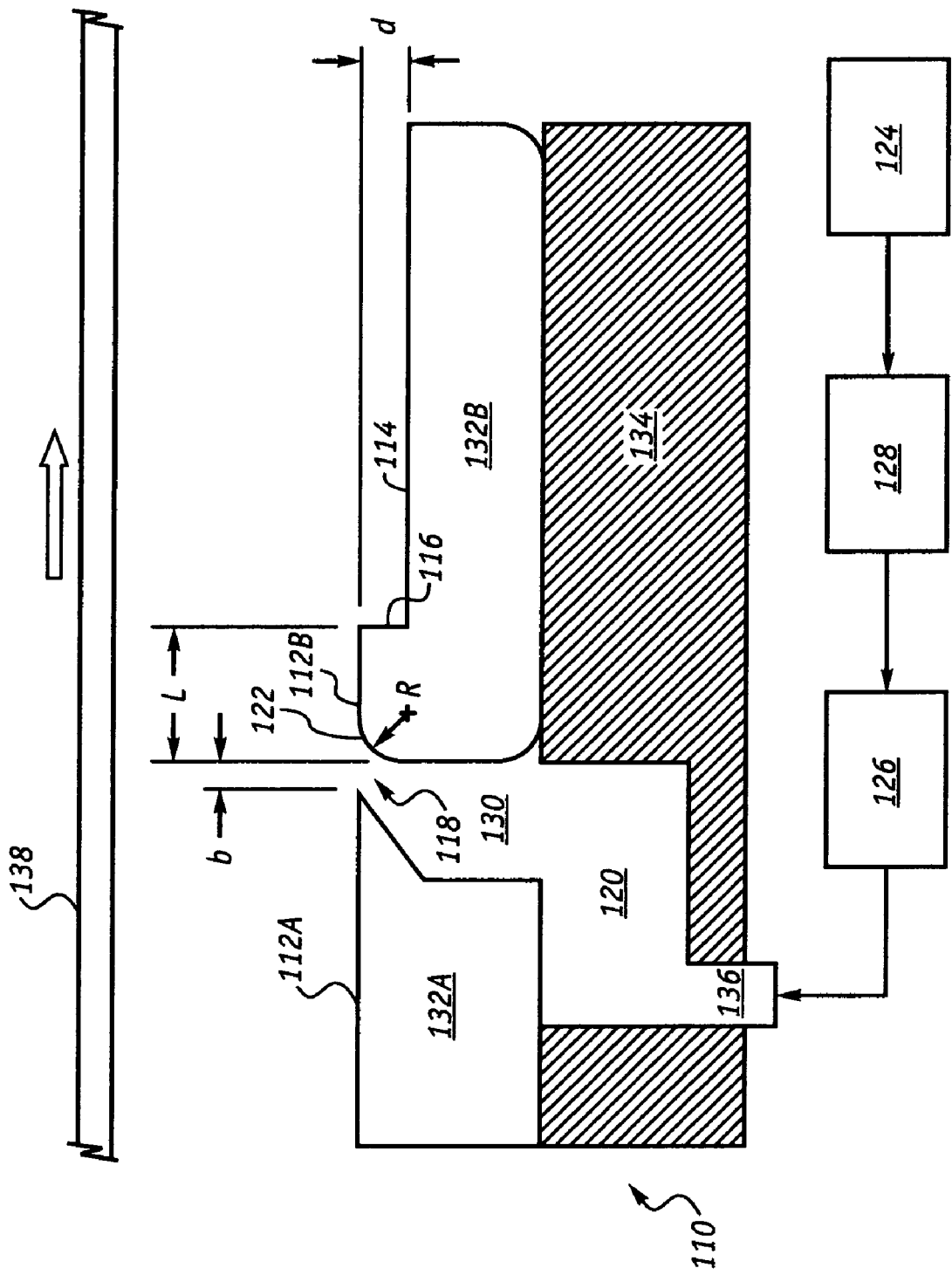
FIG. 2C is a side view of a linear air clamp stabilizer.

Instead of the above-described air-bearing stabilizer, a linear air clamp or stabilizer illustrated in FIG. 2C and which is described further in U.S. Pat. No. 6,936,137 to Moeller et al., which is incorporated herein, can be employed. With this stabilizer, a defined area of web material rides on an air bearing as the web passes over the air clamp surface. This area of the web remains flat and is parallel to the air clamp surface.

The linear air clamp stabilizer 110 includes a body with a lower portion 134 onto which upper portions 32A and 132B are attached. The body has an operative surface that is segmented into upstream upper surface 112A and downstream upper surface 112B and a lower surface 114. Upper surfaces 112A and 112B are separated by a Coanda slot 118. Upper surface 112B is disposed above lower surface 114 so that a backstep 116 is perpendicular with respect to both upper surface 112B and lower surface 114 which are typically coplanar. The stabilizer is positioned underneath a web of material 138.

Chamber 130 is connected to plenum chamber 120 which in turn is connected to a source of gas 124 via conduit 136. The volume of gas flowing into plenum 120 can be regulated by a flow meter 126 and pressure gauge 128. Conduit 136 can include a single channel which connects the source of gas 124 to plenum 120; alternatively a plurality of holes drilled into the lower surface of the stabilizer can be employed.

In operation, air is supplied to plenum 120 and a jet of gas is forced through the Coanda slot 118 which is then deflected around curved surface 122. The curvature of the jet of air then attaches to upper surface 112B and continues parallel to upper surface 112B. The jet creates a lower pressure that generates a suction force that is normal to surface 112B and an air bearing. Backstep 116 which is located downstream of the direction of the airflow extending from Coanda slot 118 promotes the creation of additional suction forces primarily through jet expand and secondarily through vortex formation, when the latter occurs.

Relative movement (in the plane of the web) of the measurement spots for the two distance determining means may be either parallel to the direction of movement of the web, that is the machine direction, perpendicular to the movement of the web in the cross direction, or some combination of the two.

When employed in a papermaking machine, the non-contacting caliper sensor is particularly suited for measuring the thickness of the finished paper near the take-up reel. The heads of the sensor are positioned on a scanner system that generally includes a pair of horizontally extending guide tracks that span the width of the paper. The guide tracks are supported at their opposite ends by upstanding stanchions and are spaced apart vertically by a distance sufficient to allow clearance for paper to travel between the tracks. The upper head and lower head are each secured to a carriage that moves back-and-forth over paper as measurements are made. Papermaking machines processes where paper is continuously manufactured from wet stock are further described, for instance, in U.S. Pat. No. 6,805,899 to MacHattie et al., U.S. Pat. No. 6,466,839 to Heaven et al., U.S. Pat. No. 6,149,770, to Hu et al., U.S. Pat. No. 6,092,003 to Hagart-Alexander et al, U.S. Pat. No. 6,080,278 to Heaven et al., U.S. Pat. No. 6,059,931 to Hu et al., U.S. Pat. No. 5,853,543 to Hu et al., and U.S. Pat. No. 5,892,679 to He, which are all incorporated herein by reference. On-line scanning sensor systems for papermaking manufacture are disclosed in U.S. Pat. Nos. 4,879,471 to Dahlquist, U.S. Pat. No. 5,094,535 to Dahlquist et al., and U.S. Pat. No. 5,166,748 to Dahlquist, all of which are incorporated herein by reference.

A caliper sensor system that was equipped with a linear air clamp and that was constructed generally as depicted in FIGS. 1A-1C and FIG. 2C was employed to measure paper thickness as the caliper sensor was scanned back and forth across the paper at the dry end of a papermaking machine. It was discovered that as the paper traversed through the space between the heads the cross-direction angle, $\theta_{CD}$, had essentially no systematic non-zero value but the sheet position parallel to the MD direction did exhibit some non-linear profile. This profile could be shifted vertically by adjusting the strength of the air pressure in the air clamp but the contour of the profile remained substantially the same. The non-linear profile exhibited a minimum point in the MD that is analogous to a trough of a wave. It is often desirable to measure the paper caliper at a minimum point of the non-linear profile, that is, the interrogation spots of the triangulation lasers should be directed to this minimum point. Unfortunately, in practice the precise location of this minimum point can only be determined after the caliper sensor has been installed; moreover, the position of this minimum point may shift in the MD over time.

With the present invention, an optical element is employed to translate the interrogation spot of a triangulation type sensor without physically moving the laser source and/or detector in the sensor head. By "optical element" is generally meant a transparent body that refracts incident light. As further described herein, it is understood that an optical element may comprise a plurality of transparent bodies in order to translate the interrogation spot. The transparent body can be made of any suitable high refractive index material, which preferably has a refractive index of about 1.5 or higher, such as, for example, quartz and plastic.

Figure 3:
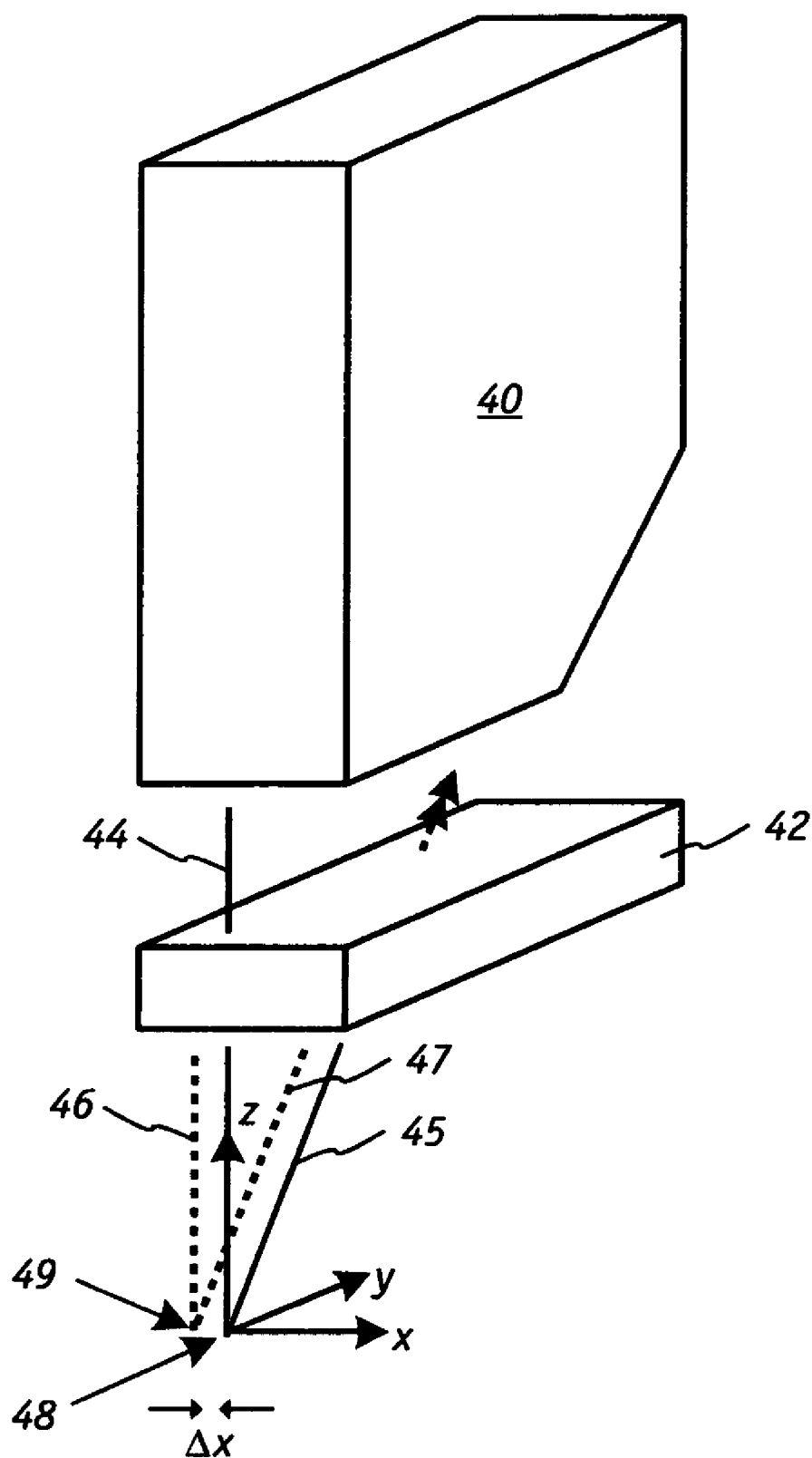
FIG. 3 is a schematic of a laser triangulation sensor with an optical element that is positioned in the beam path such that the interrogation spot is displaced in the MD direction and deflected back illustrating the triangulation geometry.

FIG. 3 depicts a head 40 of a caliper sensor with an optical element 42 that is positioned in the optical path of the emitted laser beam and the reflected laser beam. If the optical element were not present, a laser source within the head 40 projects laser beam 44 directly onto the surface of a sheet of paper (not shown) and beam 45 is reflected from the original interrogation spot 48 that is on the surface and is captured by a detector located within the head 40. For calibration purposes, the path of the non-deflected laser beam 44 is identified as the nominal path for which the laser triangulation sensor registers zero-signal, i.e., at the middle of its measurement range. The origin of the Cartesian co-ordinate system can be assigned to coincide with this reflection point 48.

When the optical element 42 is properly positioned between the head 40 and the paper, the laser beam 44 is refracted by the optical element 42 such that the beam 46 exiting the optical element 42 is projected onto the paper via a deflected path 46 so as to strike the paper at point 49 which is distance of Δx from the original reflection point 48. The reflected beam 47 is also refracted by the optical element 42. In analyzing the function of the optical element 42, the deflection can be deemed successful if sufficient flexibility in moving the interrogation spot upstream and downstream is achieved without losing a significant fraction of the measurement range. Typically, for measuring paper thickness, the triangulation of the caliper sensor is shifted, in other words, the interrogation position is displaced, in the x direction over a range (Δx) of about ±1 mm.

The optical element has a structure such that when it is introduced into the beam path of a triangulation laser sensor the deflected beam will be reflected from a displaced interrogation spot, e.g., in the MD, and deflected back in such a way that the triangulation performance of the caliper sensor is minimally affected. Preferably, an optical element can be positioned into the beam path such that the interrogation point could be shifted by a specific amount in the x-axis, so that the sheet height can be identified at different MD positions by inserting and removing the optical element from the beam path.

FIG. 3 depicts a system which includes head 40 of a caliper sensor and optical element 42 that is positioned in the optical paths of the emitted laser beam and the reflected laser beam. A caliper measurement device similar to that shown in FIG. 1A would employ two optical elements: one to optically translate the emitted laser and reflected laser beams from the upper head and the other to optically translate the emitted laser and reflected laser beams from the lower head. In this fashion, caliper measurements can be made by optically translating the laser beam from the upper head to an upper interrogation spot at a desired location on the top surface of the target while simultaneously optically translating the laser beam from the lower head to a lower interrogation spot on a location on the bottom surface of the target which is essentially immediately below that upper interrogation spot. The optical elements described herein can also be similarly deployed in this manner to yield accurate caliper or thickness measurements.

Figure 4A:
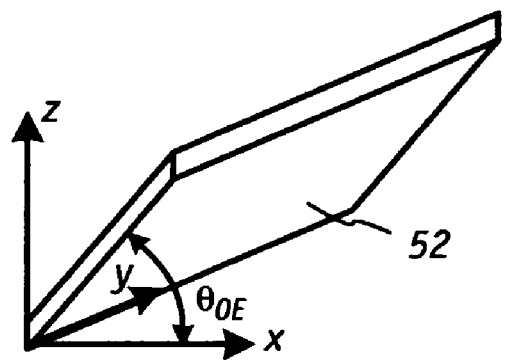
FIG. 4A is a schematic of single optical element.

FIG. 4A illustrates a single optical element 52 which can be rotated about the y axis in the x-z plane wherein the lower surface of the optical element defines angle $\theta_{OE}$ with the x axis. This configuration was analyzed to determine whether parameters can be obtained to satisfy the criterion whereby the single piece optical element provides sufficient flexibility in moving the interrogation spot upstream and downstream without losing a significant fraction of the measurement range.

Figure 4B:
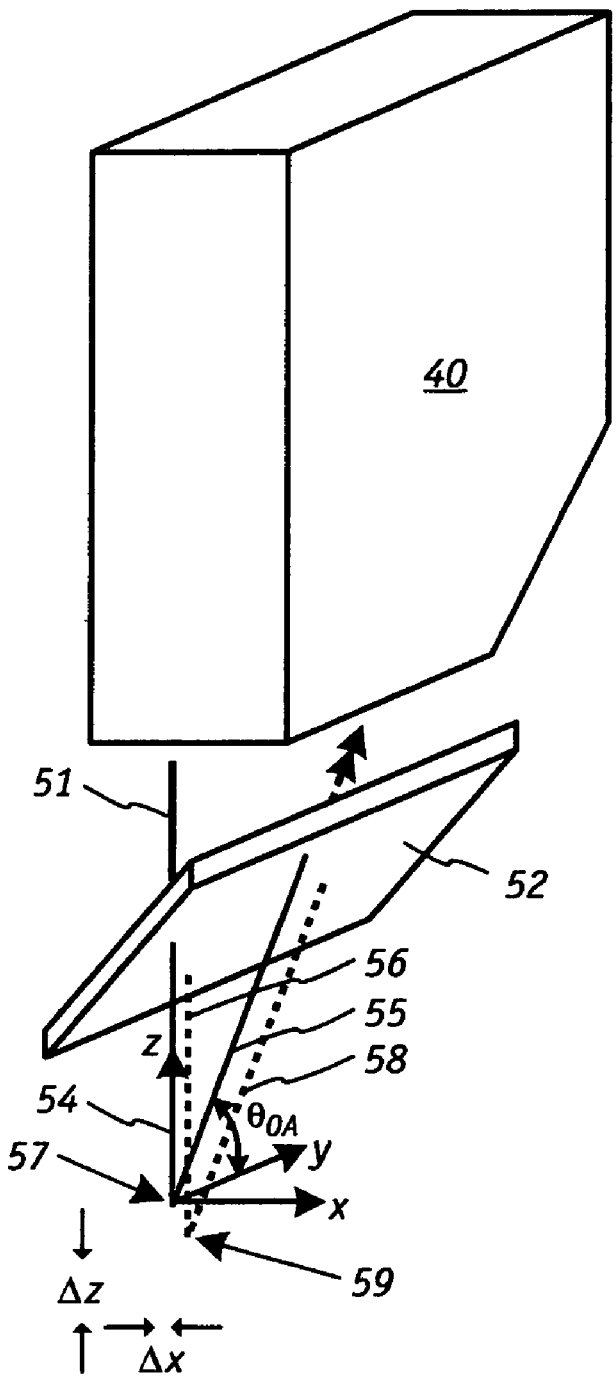
FIG. 4B shows a laser triangulation sensor with the single optical element positioned in the beam path.

FIG. 4B depicts a head 40 of a caliper sensor with the single piece optical element 52 positioned in the optical paths of the emitted laser beam and the reflected laser beam. In the absence of the optical element, a laser source within the head 40 projects laser beam 51 along path 54 directly onto the surface of a sheet of paper (not shown) and beam 55 is reflected from the original interrogation spot 57 that is on the surface and is captured by a detector located within the head 40. The nominal non-deflected path 54 has a nominal return optical axis that is in the y-z plane and makes angle $\theta_{OA}$ with the y axis. The nominal zero signal reflection position is at the origin. With the optical element 52 in place as shown, the laser beam 51 is refracted by the optical element 52 such that the beam 56 exiting the optical element 52 is projected onto the paper so as to strike the paper at point 59. The reflected beam 58 is also refracted by the optical element 52.

In analyzing the function of this single piece optical element 52, the paths of both the incident and reflected rays are considered. For the incident ray, the displacements $\Delta x_{in}$ and $\Delta z_{in}$ are calculated from the vantage point that is from the laser triangulation sensor head 40 through the optical element 52. For the reflected ray 58, a different set of displacements $\Delta_{ref}$ and $\Delta z_{ref}$ are computed from the vantage point from the detector and again downwards through the optical element. Thereafter, by varying the parameters describing the optical element such as its angle, $\theta_{OE}$, its index of refraction, $n_{OE}$, and its thickness, $h_{OE}$, a solution to the following relationship: $(\Delta x_{in}, \Delta y_{in}, \Delta z_{in}) = (\Delta x_{ref}, \Delta y_{ref}, \Delta z_{ref})$ (Equation 2) is sought. A solution to the equation means that it is possible to relocate the interrogation spot such that it is seen by the triangulation through the optical element as if it were at the nominal zero position without the optical element.

To determine the displacement in the x direction of the incident beam, using Snell's Law the following relationship can be derived:

$$\Delta x_{in} = h_{OE}\left\{\tan(\theta_{OE}) - \tan\left[\sin^{-1}\left(\frac{n_{air}\sin(\theta_{OE})}{n_{OE}}\right)\right]\right\}\cos(\theta_{OE}). \quad \text{(Equation 3.)}$$

The beam path emerges from the optical element with the same angle that it had as it entered only displaced along the x-axis. It continues straight down. Equation 3 indicates the sign of the displacement relative to the coordinates. For a positive angle, $\theta_{OE}$, a positive displacement along the x-axis is induced.

For the reflected path, the vector describing the nominal reflected principal ray as it enters the triangulation detectors is first identified. This vector will have components in the y-z plane only, $$\vec{v}_1 = \begin{pmatrix} 0 \\ \cos(\theta_{OA}) \\ \sin(\theta_{OA}) \end{pmatrix}. \quad \text{(Equation 4.)}$$

The vector normal to the optical element's upper surface, $\vec{n}_{OE}$, will have no component in the y direction, $$\vec{n}_{OE} = \begin{pmatrix} -\sin(\theta_{OE}) \\ 0 \\ \cos(\theta_{OE}) \end{pmatrix}. \quad \text{(Equation 5.)}$$

The angle between these two vectors, $\alpha_{in}$, can be found by manipulating the expression for their dot product, $\alpha_{in} = \cos^{-1}(\vec{v}_1 \cdot \vec{n}_{OE})$ (Equation 6.) and from Snell's Law the relationship between the incident angle and the refracted angle inside the optical element is known, namely:

$$\Delta_{ref}, \alpha_{ref} = \sin^{-1}\left(\frac{n_{air}\sin(\alpha_{in})}{n_{OE}}\right). \quad \text{(Equation 7.)}$$

The vector parallel to the path of the refracted ray, $\vec{v}_2$, will have a $\alpha_{ref}$ relative to $\vec{n}_{OE}$ and it will have an angle $\alpha_{in} - \alpha_{ref}$ relative to $\vec{v}_1$. If it is specified to be a unit vector, three equations in three unknowns are provided. Specifically, $$\vec{n}_{OE} \cdot \vec{v}_2 = \cos(\alpha_{ref}), \qquad \vec{v}_1 \cdot \vec{v}_2 = \cos(\alpha_{ref} - \alpha_{in}),$$
$$\text{and, } |\vec{v}_2| = 1. \qquad \text{(Equation 8.)}$$

Equation 8 can be solved for the three components of $\vec{v}_2$. Once this is done, the lateral shift of the reflected path can be found. The upper and lower planes of the optical element are first described mathematically, select an arbitrary point, $\vec{r}_0$, that lies on the upper surface. $\vec{r}_1$ will be used to denote the point at which the ray exits the lower surface, thus $\vec{r}_1$ will be described as $\vec{r}_1 = \vec{r}_0 + s\vec{v}_2$. Solve for s so that $\vec{r}_1$ lies in the lower surface. The lateral displacement will be given by $s\vec{v}_2$. Once the point $\vec{r}_1$ is determined, an identical procedure is followed to see where the reflected ray intersects with the x-z plane. This point is identified as $\vec{r}_2$, with $$\vec{r}_2 = \vec{r}_1 + s'\vec{v}_1. \qquad \text{(Equation 9.)}$$

Solving for s', the intersection of the translated reflected path with the x-z plane is determined. It is known that the translated incident path is a vertical line in the x-z plane at $\Delta x_{in}$, thus, it is possible to verify if the lateral offsets of both paths are aligned.

As an initial demonstration of the effectiveness of the present invention, a single optical element of thickness, $h_{OE}=3$ mm, optical index, $n_{OE}=1.5$, reflected optical axis inclination, $\theta_{OA}=45°$, and optical element angle, $\theta_{OE}=10°$, was employed in an attempt to manipulate the incident and reflected beams to achieve the same lateral deflection. Using Equation 2, the incident ray was laterally translated only in the +x direction by 0.177 mm. Solving for the position where the reflected ray will be located from the perspective of the detector, it was found that the reflected ray is also translated in the +x direction by 0.245 mm. This result indicated that a single optical element will not provide the same amount of lateral deflection for both incident and reflected rays. Because the reflected ray will always have a larger angle with respect to the optical element it will be subject to more lateral deflection. If a single optical element is employed, the detector will not be able to "see" the spot, although for small deflections it might be possible but the intensity will be lost resulting in measurement errors. To accommodate this effect, less lateral deflection on the return path is required.

Figures 5A, 5B:
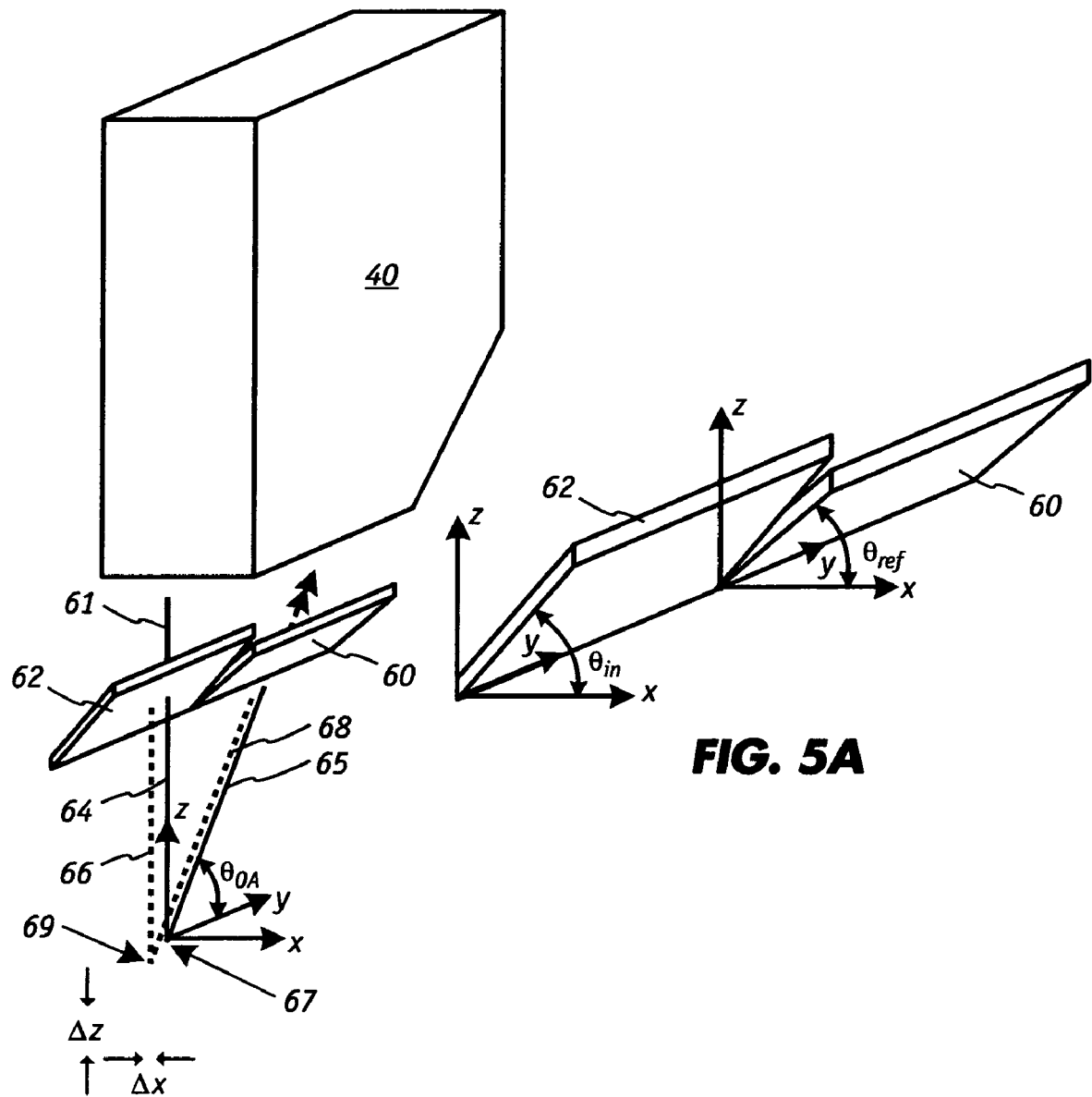
FIG. 5A is a schematic of a two piece optical element.
FIG. 5B is a schematic of a laser triangulation sensor with the two piece optical element positioned in the beam path.

In a second example, a two-piece optical element as depicted in FIG. 5A was considered. The optical element has two substrates 60, 62, e.g., two pieces of glass, each positioned at a different angle relative to the x-axis. In this arrangement, the two-piece configuration affords different angles for incident and reflected paths that are capable of providing a translated interrogation position. $\theta_{in}$ describes the optical element angle of the portion through which the incident ray path is deflected and, analogously, $\theta_{ref}$ describes the angle of the portion translating the reflected path.

FIG. 5B illustrates a head 40 of a caliper sensor with the two-piece optical element 60, 62 positioned in the optical paths of the emitter laser beam and the reflected laser beam. In the absence of the optical element, a laser source within the head 40 projects a laser beam 61 along path 64 directly onto the surface of a sheet of paper (not shown) and beam 65 is reflected from the original interrogation spot 67 that is on the surface and is captured by a detector located within the head 40. The nominal non-deflected path 64 has a nominal return optical axis that is in the x-y plane and makes angle $\theta_{OA}$ with the y axis. With the two-piece optical element in place as shown, the laser beam 61 is refracted by piece 62 and the beam path 66 which is reflected from point 69 and the reflected beam 68 is also refracted by piece 60. In the case where a web is moving in the same direction as the direction that the laser beam is optically translated, the two-piece optical element 60,62 is said to move the interrogation spot "downstream." As is apparent, by reversing the position of optical element by 180 degrees, it will optically translate the interrogation spot "upstream" in the opposite direction.

In designing a preferred a two-piece optical element that achieves a 1 mm lateral deflection, commercially available 3 mm thick windows were used. It was found that an angle of $\theta_{in}=45°$ provided a desirable $\Delta x_{in}=0.987$ mm of lateral deflection for an incident ray in accordance with Equation 2. In addition, via Equation 8, it was found that an angle of $\theta_{ref}=38.6°$ provided a similar value of lateral displacement, $\Delta x_{ref}=0.985$ mm, for the reflected path. Finally, the position at which the incident and reflected paths intersect occurred at a depth value of approximately $\Delta z=-1.32$ mm was also identified via Equation 8. The negative value of the depth intersection was expected. This meant that the zero signal position of the triangulation device is now below the original nominal position by a value of the same order as the full range, 3 mm, of the measurement device.

In principle, it is possible perform an initial nominal calibration which is done without an optical element in the beam path and thereafter acquire a second calibration with the two-piece optical element in place. A suitable calibration technique for triangulation laser based sensors is described in U.S. Pat. No. 6,967,726 to King et al., which is incorporated herein, that uses a target that is positioned on platform that can be translated in a vertical direction over the measurement ranges of the sensor. For example, the platform can include a sliding mechanism that is attached to a highly accurate stable repeatable calibrating measurement device that is used to determine very accurate indications of displacement steps during calibrations. A preferred calibrating measurement device is a calibrated linear variable differential transformer.

Figures 6A, 6B:
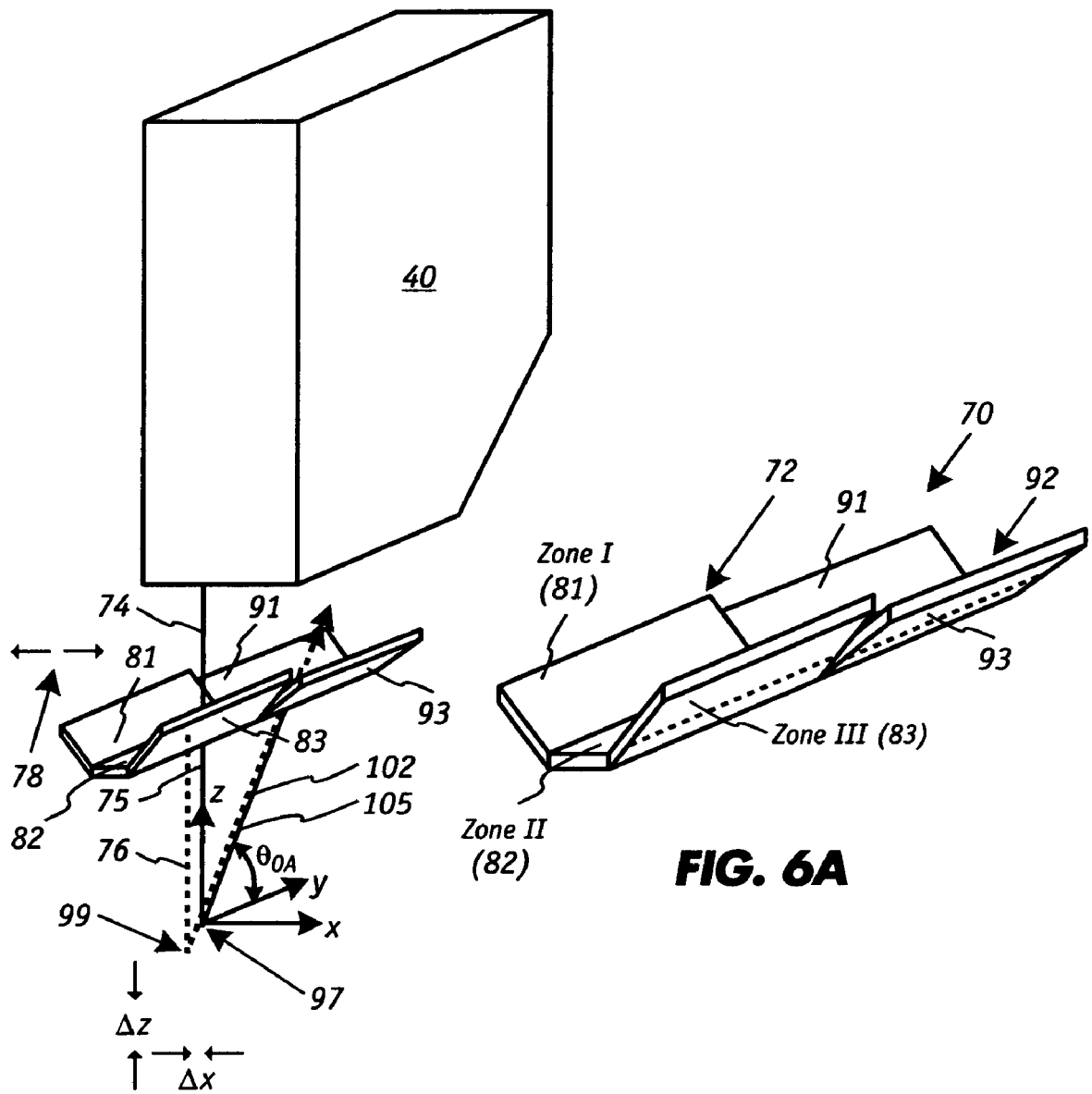
FIG. 6A is a schematic of a two piece optical element each with three zones.
FIG. 6B is a schematic of a laser triangulation sensor with the two piece-three zones optical element positioned in the beam path.

FIG. 6A depicts an embodiment of a two-piece optical element in which each piece has three zones—two plates on the sides for translating the beam in the x direction, and a neutral section or collection lens in the middle that is used to displace the zero-signal position to coincide with those of the translated rays. In particular, zone I (81) and zone I (91) can optically translate the laser beam in the x direction and similarly zone III (83) and zone III (93) can also optically translate the laser beam in the x direction. The two pieces comprising the emission and reflection plates are preferably positioned in tandem. As illustrated, piece 72 has zone I (81), zone II (82) and zone III (83) and piece 70 has zone I (91), zone II (92) and zone III (93). Although the invention is not limited by the particular dimensions of the three zones, when used in conjunction with a caliper sensor that employs laser beams that have diameters of about 1 mm, each of the three zones in both pieces 70 and 72 can be configured as a flat elongated material that is about 3 mm in thickness, 5 mm in length and 5 mm in width. In used, the plane of the upper surface of zone II (82) is preferably parallel to the plane that is defined by the lower surface of the sensor head 40. Each of zone I (81) and zone III (83) is configured so that as to define an $\theta_{in}$ of about 45°, which is the optical element angle through which an incident ray path is deflected. The emissions plates can have small CD dimensions but the reflections plates are most preferably both width and longer. If the collection lens has a diameter of approximately 1 cm, a corresponding plate which has a projected size of approximately the same size is needed.

Piece 70 is preferably positioned in tandem with piece 72 so that central zone II (82) and central zone II (92) can actually be constructed as one integral unit. In used, the plane of the upper surface of zone II (92) is preferably parallel to the plane that is defined by the lower surface of the sensor head 40. Each of zone I (91) and zone III (93) is configured so as to define an angle $\theta_{ref}$ of about 38.6° which is the optical element angle of the translating the reflected path.

FIG. 6B illustrates the upper head 40 of a caliper sensor with a two-piece 72, 70 optical element which is positioned in the optical paths of the laser beam and the reflected laser beam. The optical element can be mounted to head 40. In the absence of the optical element, a laser source within the head 40 projects a laser beam 74 along path 75 directly onto the surface of a sheet of paper (not shown) and beam 105 is reflected from the original interrogation spot 97 that is on the surface and is captured by a detector located within the head 40. The nominal non-deflected path 74 has a nominal return optical axis that is in the x-y plane and makes angle $\theta_{OA}$ with the y axis. With the two-piece optical element in place, the deflected beam 76 reflected from the interrogation spot 99 that is on the surface and the reflected beam 102 is captured by a detector located within the head 40. By translating the optical element parallel to the x-axis as depicted by reference character 78, the interrogation position is translated along the x-axis which is parallel to the machine direction in which a sheet of paper is moving.

An optical element must be properly calibrated. For the two-piece device of FIG. 6A, this can be achieved by positioning the optical element such that the triangulation is performed at multiple positions of a calibration target through zone I. Data are acquired and the calibration stored. Similar calibrations procedures are implemented for zones II and III.

With the two-piece optical element device of FIG. 6A, zone I of piece 70 and zone I of piece 72 are employed during normal operations of the caliper sensor such that the incident and reflected light will travel through these two zones as the caliper sensor is scanned back and forth across the moving target such as a web of paper. If the web shifts so that the interrogation spot is no longer at an optimal point for caliper measurements, then the other zones of the optical element are also employed to measure or probe multiple web positions in order to locate a new interrogation spot for the caliper measurements. Specifically, the optical element is maneuvered to ascertain signal measurements in each of each of the three zones and the respective calibrations are used to determine the displacements measured at each of the three zones. The sheet heights are estimated for three positions and in increments upstream and downstream along with the nominal measurement With the invention, it is possible to ascertain that the measurement position is suboptimal due to an increased error in measurement—specifically an error which correlates with y displacement. If this is detected, then other positions should be tried. Alternatively, the plates can be periodically moved to interrogate the upstream and downstream positions to determine if the measurement position is still in the ideal position.

Typically, an interrogation spot that is at a minimum or flat region of a moving web is desirable since accurate caliper measurements can be achieved when the triangulation laser beams are directed at this interrogation spot. Once this new interrogation spot is determined, the caliper sensor can be physically moved so that the interrogation spots of the incident laser beams from the upper and lower sensor heads are directed at this new interrogation spot. Alternatively, the pressure of an air clamp can be adjusted to move the moving web itself, as the caliper sensor remains stationary, so that the incident laser beams reflect off this interrogation spot.

The plates or zones as depicted in FIGS. 6A and 6B need not be fixed. For instance, motor-driven plates could be employed to scan a range of MD positions. In this case, only two independently driven plates are required; a look-up table can be used to correlate the angle of the first plate to that of the second.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A triangulation sensing device for measuring the distance from a target that comprises:

a sensor head that is disposed adjacent the target wherein the sensor head includes (i) a source of incident radiation that emits incident radiation along a first path and (ii) means for detecting reflected radiation from an interrogation spot on a surface of the target;

means for optically translating the incident radiation that comprises a first transparent optical element which is positioned in the first path and between the sensor head and the target wherein incident radiation is refracted by the first transparent optical element such that incident radiation exiting the first transparent optical element is directed along a second path toward an interrogation spot on a surface of the target from where radiation is reflected along on a third path and wherein the first path has a direction that is different from that of the second path; and means for optically translating the reflected radiation from the interrogation spot that comprises a second transparent optical element which is positioned in the third path and between the sensor head and the target wherein reflected radiation is refracted by the second transparent optical element such that the reflected radiation that exits the second transparent optical element travels along a fourth path and is detected by the means for detecting reflected radiation and wherein the third path has a direction that is different from that of the fourth path.

2. The triangulation sensing device of claim 1 wherein the means for optically translating the incident radiation comprises a first substrate and the means for optically translating the reflected radiation comprises a second substrate.

3. The triangulation sensing device of claim 2 wherein the first substrate is substantially planar and the second substrate is substantially planar wherein the first substrate is not coplanar with the second substrate.

4. The triangulation sensing device of claim 2 wherein the first substrate comprises a first zone, second zone and a third zone and the second substrate comprises a corresponding first zone, second zone and third zone characterized in that: (i) when incident radiation is optically translated by the first zone of the first substrate the reflected radiation is optically translated by the first zone of the second substrate (ii) when incident radiation is optically translated by the second zone of the first substrate the reflected radiation is optically translated by the second zone of the second substrate, and (iii) when incident radiation is optically translated by the third zone of the first substrate the reflected radiation is optically translated by the third zone of the second substrate.

5. The triangulation sensing device of claim 1 further comprising means for analyzing the reflected radiation to determine the distance from the sensor head to the target.

6. the triangulation sensing device of claim 1 wherein the source of incident radiation is a laser.

7. A system, for measurement of the thickness of a target having a first surface and a second surface, that comprises:
   a first sensor head that is disposed adjacent the first surface of the target wherein the first sensor head includes (i) a first source of first incident radiation that emits a first incident radiation along a first path and (ii) first means for detecting first reflected radiation from a first interrogation spot on the first surface of the target;
   means for optically translating the first incident radiation that comprises a first transparent optical element which is positioned in the first path and between the first sensor head and the target wherein the first incident radiation is refracted by the first transparent optical element such that first incident radiation exiting the first transparent optical element is directed along a second path toward a first interrogation spot on the first surface of the target from where radiation is reflected along a third path and wherein the first path has a direction that is different from that of the second path;
   means for optically translating a first reflected radiation from the first interrogation spot that comprises a second transparent optical element which is positioned in a third path and between the first sensor head and the target wherein the first reflected radiation is refracted by the second transparent optical element such that first reflected radiation that exits the second transparent optical element travels along a fourth and is detected by the first means for detecting first reflected radiation and wherein the third path has a direction that is different from that of the fourth path;
   a second sensor head that is disposed adjacent the second surface of the target wherein the second sensor head includes (i) a second source of second incident radiation that emits a second incident radiation along a fifth path and (ii) second means for detecting second reflected radiation from a second interrogation spot on the second surface of the target;
   means for optically translating the second incident radiation that comprises a third transparent optical element which is positioned in the fifth path and between the second sensor head and the target wherein the second incident radiation is refracted by the second optical element such that second incident radiation exiting the third optical element is directed along a sixth path toward the second interrogation spot on the second surface of the target from where radiation is reflected along a seventh path and wherein the fifth path has a direction that is different from that of the sixth path;
   means for optically translating a second reflected radiation from the second interrogation spot that comprises a fourth trans parent optical element which is positioned in the fifth path and between the second sensor head and the target wherein the second reflected radiation is refracted by the fourth transparent optical element such that second reflected radiation that exits the fourth transparent element travels along an eighth path and is detected by the second means for detecting second reflected radiation and wherein the seventh path has a direction that is different from that of the eighth path; and
   means for measuring the distance from the first sensor head to the second sensor head.

8. The system of claim 7 wherein first interrogation spot on the first surface of the target is essentially immediately above or below the second interrogation spot on the second surface of the target.

9. The system of claim 7 wherein the means for optically translating the first incident radiation comprises a first substrate and the means for optically translating the first reflected radiation comprises a second substrate and wherein the means for optically translating the second incident radiation comprises a third substrate and the means for optically translating the second reflected radiation comprises a fourth substrate.

10. The system of claim 9 wherein the first substrate is substantially planar and the second substrate is substantially planar wherein the first substrate is not coplanar with the second substrate and wherein the third substrate is substantially planar and the fourth substrate is substantially planar wherein the third substrate is not coplanar with the fourth substrate.

11. The system of claim 9 wherein (a) the first substrate comprises a first zone, second zone and a third zone and the second substrate comprises a corresponding first zone, second zone and third zone characterized in that: (i) when incident radiation is optically translated by the first zone of the first substrate the reflected radiation is optically translated by the first zone of the second substrate (ii) when incident radiation is optically translated by the second zone of the first substrate the reflected radiation is optically translated by the second zone of the second substrate, and (iii) when incident reflected radiation is optically translated by the third zone of the first substrate the reflected radiation is optically translated by the third zone of the second substrate and (b) wherein the third substrate comprises a first zone, second zone and a third zone and the fourth substrate comprises a corresponding first zone, second zone and third zone characterized in that: (i) when incident radiation is optically translated by the first zone of the third substrate the reflected radiation is optically translated by the first zone of the fourth substrate (ii) when incident radiation is optically translated by the second zone of the third substrate the reflected radiation is optically translated by the second zone of the fourth substrate, and (iii) when incident radiation is optically translated by the third zone of the third substrate the reflected radiation is optically translated by the third zone of the fourth substrate.

12. The system of claim 7 further comprising means for analyzing the reflected first and second radiations to determine the distances from the first and second sensor heads to the first and second surfaces of the target, respectively.

13. The system of claim 7 wherein each of the first and second sources of incident radiation is a laser.

14. A method of determining the position of a target that comprises the steps of:
   (a) providing a triangulation sensing device, for measuring distance that comprises a sensor head, that is disposed adjacent the target wherein the sensor head includes (i) a source of incident radiation that emits incident radiation along a first path and (ii) means for detecting reflected radiation from an interrogation spot on a surface of the target;
   (b) positioning a first transparent optical element in the first path whereby the incident radiation is refracted by the first transparent optical element such that incident radiation exiting the first transparent optical element is directed along a second path toward an interrogation spot on the target surface from where radiation is reflected along a third path and wherein the first path has a direction that is different from that of the second path;

(c) positioning a second transparent optical element in the third path whereby the reflected radiation from the interrogation spot is refracted by the second transparent optical element such that reflected radiation that exits the second transparent optical element travels along a fourth path and is detected by the means for detecting reflected radiation and wherein the third path has a direction that is different from that of the fourth path; and (d) determining the position of the interrogation spot.

15. The method of claim 14 wherein step b employs a first substrate to refract the incident radiation and the step c employs a second substrate to refract the reflected radiation.

16. The method of claim 15 wherein the first substrate is substantially planar and the second substrate is substantially planar wherein the first substrate is not coplanar with the second substrate.

17. The method of claim 15 wherein the first substrate comprises a first zone, second zone and a third zone and the second substrate comprises a corresponding first zone, second zone and third zone characterized in that: (i) when incident radiation is optically translated by the first zone of the first substrate the reflected radiation is optically translated by the first zone of the second substrate (ii) when incident radiation is optically translated by the second zone of the first substrate the reflected radiation is optically translated by the second zone of the second substrate, and (iii) when incident radiation is optically translated by the third zone of the first substrate the reflected radiation is optically translated by the third zone of the second substrate.

18. The method of claim 14 wherein step d comprises analyzing the reflected radiation to determine the distance from the sensor head to the target.

19. The method of claim 14 further comprising repeating steps b, c, and d to determine the positions of a plurality of interrogations spots on the target.

20. The method of claim 11 wherein the target comprises a moving web.

21. The triangulation sensing device of claim 1 wherein the first transparent optical element and the second transparent optical element are formed as an integral structure.

22. The system of claim 7 wherein the first transparent optical element and the second transparent optical element are formed as an integral structure and wherein the third transparent optical element and the fourth transparent optical element are formed as an integral structure.

23. The method of claim 14 wherein the first transparent optical element and the second transparent optical element are formed as an integral structure.

* * * * *